United States Patent
Shimada et al.

(10) Patent No.: US 8,580,955 B2
(45) Date of Patent: Nov. 12, 2013

(54) PURIFICATION METHOD AND PRODUCTION METHOD FOR CELLOBIOSE

(75) Inventors: Kensaku Shimada, Osaka (JP); Takashi Ichihara, Kobe (JP); Takahiko Tsumiya, Nagaokakyo (JP); Yasuhiro Takami, Akashi (JP); Mikie Fukushima, Ibaraki (JP)

(73) Assignees: Matsutani Chemical Industry Co., Ltd., Hyogo (JP); Japan Chemical Engineering & Machinery Co., Ltd., Osaka (JP)

( * ) Notice: Subject to any disclaimer, the term of this patent is extended or adjusted under 35 U.S.C. 154(b) by 613 days.

(21) Appl. No.: 11/911,146

(22) PCT Filed: Apr. 12, 2006

(86) PCT No.: PCT/JP2006/307726

§ 371 (c)(1), (2), (4) Date: Oct. 10, 2007

(87) PCT Pub. No.: WO2006/112316

PCT Pub. Date: Oct. 26, 2006

(65) Prior Publication Data

US 2009/0281305 A1    Nov. 12, 2009

(30) Foreign Application Priority Data

Apr. 13, 2005 (JP) .................................. 2005-116054

(51) Int. Cl.
*C07H 1/06*  (2006.01)
*C07H 3/04*  (2006.01)

(52) U.S. Cl.
USPC ......................................................... 536/128

(58) Field of Classification Search
None
See application file for complete search history.

(56) References Cited

U.S. PATENT DOCUMENTS 6,680,048 B2 *  1/2004  Grainger et al. ................ 424/65

FOREIGN PATENT DOCUMENTS

| | | | |
|---|---|---|---|
| JP | 63-226294 A | 9/1988 | |
| JP | 3-31294 A | 2/1991 | |
| JP | 05-317073 | * 12/1993 | ............. C12P 19/14 |
| JP | 5-317073 A | 12/1993 | |
| JP | 07-184678 | * 7/1995 | ............. C12P 19/14 |
| JP | 7-184678 A | 7/1995 | |
| JP | 8-89274 A | 4/1996 | |
| JP | 9-107987 A | 4/1997 | |
| JP | 2005-68140 A | 3/2005 | |
| WO | WO 03/085139 A1 | 10/2003 | |

OTHER PUBLICATIONS

Oxford English Dictionary at AskOxford.com "rate"; also available at http://www.askoxford.com/concise_oed/rate_1?view=uk; last viewed Nov. 10, 2009.*
Faria, N. et al., Powder Technology "Quantification of the morphology of sucrose crystals by image analysis", vol. 133, pp. 54-67 (2003).*
Miller, "Hydrolysis of Cellulose to Oligosaccharides," *Methods in Carbohydrate Chemistry III*:134-139, Academic Press (1963).
Sowden et al., "The Isolation of 5-O-β-D-Glucopyranosyl-D-glucose from Hydrol", J. Am. Chem. Soc., 1956, v. 78, pp. 2503-2505.

* cited by examiner

*Primary Examiner* — Layla Bland
*Assistant Examiner* — Bahar Craigo
(74) *Attorney, Agent, or Firm* — Sughrue Mion, PLLC

(57) ABSTRACT

The present invention provides a method for purifying cellobiose which comprises the steps of (A) preparing a cellobiose-containing sugar solution; (B) increasing the rate of cellobiose present in the sugar solution relative to the total saccharides present therein up to at least 50% by mass; and (C) crystallizing cellobiose; and a method for preparing cellobiose having a high content of the α-anomer thereof which comprises the step of drying a cellobiose-containing sugar solution having a rate of cellobiose of at least 90% by mass relative to the total saccharides present therein while maintaining the sugar solution at a temperature ranging from 80 to 95° C. These methods of the present invention permit the economical preparation of cellobiose having considerably improved purity and recovery rate, without using any complicated process. Moreover, the present invention also permits the preparation of cellobiose highly soluble in water.

5 Claims, No Drawings

PURIFICATION METHOD AND PRODUCTION METHOD FOR CELLOBIOSE

TECHNICAL FIELD

The present invention relates to a method for recovering highly pure cellobiose from a cellobiose-containing sugar solution in a high yield and at a low cost and a method for the preparation of cellobiose having a high solubility in water.

BACKGROUND ART

Cellobiose is a disaccharide produced through the hydrolyzation process of cellulose widely distributed in, for instance, plants and has such a structure that two glucose molecules are linked through β-1,4 bond. Cellobiose is a naturally occurring material present in, for instance, stems of maize and pine needles and has a sweet taste, but it is not hydrolyzed by human. Accordingly, if cellobiose may efficiently and economically be prepared, it would be considered to be useful as a sweetening agent for use in health foods and foods for patients suffering from diabetes or a raw material for preparing cosmetic products and medicines.

As a conventionally known method for preparing cellobiose, there have been proposed those in which cellulose is chemically or enzymatically hydrolyzed.

Among them, examples of such enzymatic hydrolyzation methods include those comprising reacting cellulose with commercially available cellulase formulations containing cellulase originated from, for instance, microorganisms such as those belonging to the genus *Trichoderma* and *Aspergillus* to thus give cellobiose, as well as a method in which cellobiose is prepared using enzyme formulations from which β-glucosidase has been removed, while making use of the difference in the adsorbing power of cellulase to cellulose (Patent Document 1) and a method in which the hydrolysis reaction of cellulose is carried out in the presence of lignin (Patent Document 2). Moreover, there has also been known a method for the purification of cellobiose as an improved technique of the foregoing ones, which comprises hydrolyzing lignocellulose in the presence of a cellulase and a lignin-hydrolyzing bacterium or a lignin-hydrolyzing enzyme (Patent Document 3). However, the sugar solutions prepared through the hydrolysis according to these methods contain, in themselves, a large quantity of monosaccharides such as glucose and cello-oligosaccharides and accordingly, they cannot be considered to be highly pure cellobiose and the methods are likewise unsatisfied in the yields of cellobiose. In addition, if the content of glucose which is mixed in the sugar solution increases, it is expected that cellobiose is hardly crystallized.

On the other hand, as the foregoing chemical hydrolyzation techniques, there has been known, for instance, a method in which cellobiose is fractionated and isolated through the use of, for instance, a carbon column (Non-patent Document 1), but this method requires the use of quite complicated operations, including the use of a carbon column having a large volume and a large amount of ethanol for the elution from the column. Moreover, the method does not provide cellobiose in a satisfactorily high yield, it accordingly leads to a considerable increase in the production cost of cellobiose and the resulting product cannot accordingly be used in the field of foods. In addition, cellobiose has not yet been mass-produced industrially and accordingly, it has simply been prepared in a very small scale only for a reagent. There has recently been developed a method for preparing cellobiose (Patent Document 4), which comprises the steps of cooking and digesting a raw material containing naturally occurring lignocellulose and then partially hydrolyzing wet pulp thus obtained without using any drying step, by the action of a cellulase. This method comprises the steps of acting a cellulase on un-dried wet pulp which is quite susceptible to the action of the cellulase as a substrate, in a hydrolysis system equipped with an ultrafiltration membrane and continuously removing the hydrolyzation products from the reaction system through filtration and the method has thus been successful in the production of a cellobiose-containing sugar solution in a high yield. In addition, there has likewise been proposed a method for purifying cellobiose according to the same principle used in the foregoing method while using, as a raw material, bleached slush pulp (Patent Document 5).

However, the sugar solutions prepared according to these methods have high contents of glucose, oligosaccharides and other impurities and therefore, they cannot be used for the preparation of high purity cellobiose without using any further treatment.

Patent Document 1: JP-A-63-226294;
Patent Document 2: JP-A-05-317073;
Patent Document 3: JP-A-08-89274
Patent Document 4: JP-A-07-184678
Patent Document 5: JP-A-09-107987
Non-Patent Document 1: Miller, g. L., Methods in Carbohydrate Chemistry III, 1963, p. 134 (Academic Press).

DISCLOSURE OF THE INVENTION

Problems to be Solved by the Invention

Accordingly, it is an object of the present invention, in consideration of the present status of the foregoing techniques, to provide a method for economically purifying cellobiose, which permits the achievement of considerably improved purity and recovery, starting from synthesized cellobiose or a cellobiose-containing sugar solution obtained through the hydrolyzation of cellulose, without using any complicated processes.

It is another object of the present invention to provide a method for the preparation of cellobiose having high solubility in water.

Means for the Solving the Problems

The inventors of this invention have conducted various studies of methods for purifying cellobiose and as a result, have found that cellobiose can easily be separated in the form of crystals thereof by subjecting a cellobiose-containing sugar solution, whose ratio of cellobiose relative to the total amount of the saccharides present in the sugar solution is increased to at least a predetermined level, to desalting and decoloring treatments and that highly pure cellobiose can easily be obtained through the collection of the resulting crystals thereof. Moreover, the inventors have further found that high purity cellobiose can be obtained at a further improved recovery by fractionating the foregoing cellobiose-containing sugar solution using a strongly acidic cation-exchange resin to thus increase the cellobiose concentration of the solution and then crystallizing the cellobiose present in the solution. Furthermore, the inventors have likewise found that cellobiose powder whose solubility in water is further improved as compared with the solubility of the original crystals of cellobiose can be obtained when warming the sugar solution thus obtained and containing cellobiose in a higher concentration at a specific temperature and then converting the same into powder without using any additional treatment. The present invention has thus been developed on the basis of the foregoing findings.

The present invention provides the following method for purifying cellobiose and a method for preparing cellobiose.

1. A method for purifying cellobiose comprising the steps of (A) preparing a cellobiose-containing sugar solution; (B) increasing the ratio of cellobiose present in the sugar solution relative to the total saccharides present therein up to at least 50% by mass; and (C) crystallizing the cellobiose present in the solution.
2. The method for purifying cellobiose as set forth in the foregoing item 1, wherein the ratio of cellobiose present in the sugar solution relative to the total saccharides present therein is increased up to at least 60% by mass.
3. The method for purifying cellobiose as set forth in the foregoing item 1 or 2, wherein the step (B) comprises a step of ultrafiltration.
4. The method for purifying cellobiose as set forth in the foregoing item 3, wherein the step (B) further comprises a step of concentrating the sugar solution through the use of a reverse osmosis membrane after the ultrafiltration step.
5. The method for purifying cellobiose as set forth in the foregoing item 3, wherein the step (B) further comprises a step of fractionating the sugar solution using a strongly acidic cation-exchange resin after the ultrafiltration step.
6. The method for purifying cellobiose as set forth in any one of the foregoing items 1 to 5, wherein the step (A) comprises steps of cooking and digesting a raw material containing naturally occurring lignocellulose and then partially hydrolyzing un-dried wet pulp thus obtained by the action of a cellulase.
7. A method for preparing cellobiose having a high content of the α-anomer thereof comprising the step of drying a sugar solution having a ratio of cellobiose of at least 90% by mass relative to the total saccharides present therein while maintaining the solution at a temperature ranging from 80 to 95° C.
8. The method for preparing cellobiose as set forth in the foregoing item 7, wherein the cellobiose-containing sugar solution is a solution obtained by re-dissolving cellobiose crystals.
9. The method for preparing cellobiose as set forth in the foregoing item 7, wherein the drying step is any one of spray-drying, drum-drying or extruder processing.
10. The method for preparing cellobiose as set forth in any one of the foregoing items 7 to 9, wherein the cellobiose-containing sugar solution is one obtained by cooking and digesting a raw material containing naturally occurring lignocellulose and then partially hydrolyzing un-dried wet pulp thus obtained by the action of a cellulase.

Effects of the Invention

The purification method of the present invention permits the economical preparation of highly purified cellobiose in a high yield. In addition, the preparation method of the present invention permits the economical preparation of highly purified cellobiose, in a high yield, which has a high content of the α-anomer thereof and a high solubility in water. Accordingly, the cellobiose prepared according to the present invention can be expected as a natural non-digestible sweetening agent which can be used in various fields of foods such as health foods and foods for patients suffering from diabetes. In addition, it may likewise be used as a raw material for cosmetic formulations as well as medicines.

BEST MODE FOR CARRYING OUT THE INVENTION

The present invention relates to a method for purifying cellobiose comprising the steps of (A) preparing a cellobiose-containing sugar solution; (B) increasing the ratio of cellobiose present in the sugar solution relative to the total saccharides present therein up to at least 50% by mass; and (C) crystallizing the cellobiose present therein.

The cellobiose-containing sugar solution used in the present invention can be prepared by any known method such as one disclosed in the foregoing Patent Document 4. More specifically, an acetic acid buffer having a pH value of 5.5 is added to un-dried wet un-bleached sulfite pulp which is obtained by cooking and digesting a naturally occurring lignocellulose-containing raw material to thus prepare a 2% by mass slurry. Then the slurry thus prepared is introduced into a bio-reactor equipped with an ultrafiltration membrane, the slurry is heated to a temperature of 45° C. while circulating the same with a pump, the cellulase originated from a microorganism belonging to *Trichoderma viride* is added to the slurry in a concentration of 0.1% by mass on the basis of the total mass of the slurry, while maintaining the slurry at that temperature, to hydrolyze the cellulose through the enzyme reaction carried out for 4 hours and to thus obtain a cellobiose-containing sugar solution.

Alternatively, it is also possible to use the method as disclosed in the foregoing Patent Document 5 as a further method for the preparation of such a cellobiose-containing sugar solution.

Then the ratio of cellobiose present in the sugar solution relative to the total mass of the saccharides present therein is controlled to a level of not less than 50% by mass.

For example, the hydrolysis reaction solution which has been treated by passing the same through the foregoing ultrafiltration membrane can be concentrated without any further treatment or it can likewise be concentrated using a reverse osmosis membrane having a low blocking rate to thus adjust the ratio of cellobiose present in the sugar solution relative to the total mass of the saccharides to a level of not less than 50% by mass. The "reverse osmosis membrane having a low blocking rate" used herein is also referred to as a "loose RO membrane" and it is not restricted to any specific one insofar as the reverse osmosis membrane has such a function that most of glucose molecules can pass through the membrane, but most of cellobiose cannot pass through the same. By way of example, there can be listed NTR-7250 available from Nitto Denko Corporation.

The ratio of cellobiose present in the sugar solution thus prepared relative to the total mass of the saccharides present therein is not less than 50% by mass, and preferably not less than 60% by mass. This is because, the use of a cellobiose-containing sugar solution having a ratio of cellobiose of less than 50% by mass would lead to the reduction of the recovery of crystals in the subsequent crystallization step. In other words, the glucose present in the sugar solution would inhibit the crystallization of cellobiose and accordingly, the content of glucose present in the sugar solution is preferably lower than that of cellobiose.

It is preferred that the cellobiose-containing sugar solution is subjected to a decoloring treatment according to any appropriate means such as one using activated carbon and a desalting treatment according to any appropriate means such as one using an ion-exchange resin. These steps can facilitate the subsequent crystallization step. In this respect, it is preferred that the cellobiose-containing sugar solution thus subjected to the foregoing decoloring and desalting treatments is concentrated till the cellobiose concentration exceeds 14% (w/v). The use of a cellobiose-containing sugar solution having a cellobiose concentration of less than 14% (w/v) would lead to the reduction of the recovery of crystals in the subsequent step.

Glucose, oligosaccharides and other impurities, which may inhibit the crystallization of cellobiose, can, if necessary, be removed from the sugar solution by treating the sugar solution with, for instance, an ion-exchange resin. For instance, a cellobiose-containing sugar solution is passed through a column packed with a strongly acidic cation-exchange resin (an Na-type or Ca-type one), followed by the elution thereof with water to thus separate glucose, oligosaccharides and other impurities from the sugar solution. If preparing, according to such a method, a cellobiose-containing sugar solution whose cellobiose concentration and purity have further been improved, highly purified cellobiose crystals can be obtained in a high yield.

Accordingly, if concentrating the cellobiose-containing sugar solution having a ratio of cellobiose of not less than 50% by mass relative to the total mass of the saccharides present in the solution, cellobiose is separated from the solution through the crystallization thereof and a cellobiose crystal-containing slurry can thus be prepared with ease. The crystals of cellobiose thus separated out of the sugar solution can be recovered or collected by any known means such as a filtration or centrifugation treatment. It is also possible to optionally recrystallize the cellobiose crystals obtained above. The crystals thus recovered are washed with a small amount of cold water and/or water-containing ethanol and then dried.

The purity and recovery of the resulting cellobiose crystals may vary depending on the characteristics of the cellobiose-containing sugar solution used, but it is common that they are not less than 93% by mass and not less than 40% by mass, respectively. In this connection, the cellobiose content can be determined by a high performance liquid chromatography (HPLC) technique.

According to another aspect of the present invention, there is also provided a method for preparing cellobiose having a high content of the α-anomer thereof which comprises the step of drying a cellobiose-containing sugar solution having a cellobiose content of at least 90% by mass relative to the total mass of the saccharides present therein while maintaining the sugar solution at a temperature ranging from 80 to 95° C.

The solubility (the rate of dissolution) of crystalline cellobiose in water may vary depending on the rates of the stereoisomers (the rates of the α- and β-anomers). For instance, when the cellobiose crystals are dissolved in water, the resulting solution is maintained at a high temperature falling within the range in which the solution is not boiled, preferably 80 to 95° C. for a time ranging from 0.5 to 2.0 hours and then the solution is dried while maintaining the same at that temperature, the ratio of the α-anomer is increased to thus give cellobiose powder improved in its solubility in water. The "solubility" used herein can, for instance, be evaluated on the basis of the time required for the complete dissolution of a sample in water, observed when 10 g of the sample is added to 100 mL of water maintained at 25° C., with stirring.

The method for drying the cellobiose solution is not restricted to any particular one, but specific examples thereof include a spray-drying method, a drum-drying method and an extruder processing technique.

The cellobiose product whose solubility is improved can likewise be prepared without using any crystallization step. More specifically, a cellobiose-containing sugar solution whose cellobiose content has been increased to a level of not less than 90% by mass through the fractionation operation using a strongly acidic cation-exchange resin is subjected to a drying step according to the same procedures used above, to thus permit the preparation of a cellobiose product having a higher solubility in water as compared with that of the crystals prepared through the crystallization treatment.

The present invention will hereunder be described in more detail with reference to the following test examples, and working examples, but the present invention is by no means limited to these specific examples at all.

Test Example 1

Determination of Solubility of Cellobiose

There was prepared a 20% (w/v) solution of a commercially available cellobiose (manufactured by Wako Pure Chemical Co., Ltd.), the resulting solution was introduced into a thermostatic chamber maintained at a temperature ranging from 10 to 60° C. to thus form crystals of cellobiose, thereafter the content of water present in the supernatant was determined using a Karl Fisher moisture meter and then the solubility was calculated by subtracting the moisture content from 100%.

TABLE 1

| Temperature (° C.) | Solubility of Cellobiose (%) |
|---|---|
| 10 | 13.5 |
| 20 | 14.0 |
| 30 | 14.7 |
| 40 | 18.4 |
| 50 | 22.9 |
| 60 | 26.3 |

The results listed in foregoing Table 1 suggest that when separating cellobiose crystals from a cellobiose-containing sugar solution, the sugar solution should be concentrated till the cellobiose concentration of the sugar solution exceeds at least 14% (w/v), for instance, at a temperature of 20° C.

Test Example 2

Effect of Glucose on Crystallization of Cellobiose

Cellobiose (available from Wako Pure Chemical Co., Ltd.) was blended with glucose (available from Kishida Chemical Co., Ltd.) to thus give solutions of Brix 40 and 50 respectively such as those shown in the following Table 2, each of these solutions was allowed to stand at 20° C. for 90 hours and the presence of crystals was evaluated with naked eyes. In addition, the samples whose crystals could be recovered were inspected for the purity of cellobiose according to the high performance liquid chromatography.

TABLE 2

| Amt. of cellobiose in sugar solution prepared, g (%) | Amt. of glucose in sugar solution prepared, g (%) | Amt. of sugar solution prepared, g (Brix) | Presence of crystals after 90 hrs. * | Purity of cellobiose crystals (%) |
|---|---|---|---|---|
| 24 (80) | 6 (20) | 75 (40) | A | 96.5 |
| 24 (60) | 16 (40) | 80 (50) | A | 88.1 |
| 24 (60) | 16 (40) | 100 (40) | B | 92.7 |
| 24 (50) | 24 (50) | 96 (50) | A | 86.0 |
| 24 (50) | 24 (50) | 120 (40) | C | — |
| 24 (40) | 36 (60) | 120 (50) | B | — |
| 24 (40) | 36 (60) | 150 (40) | C | — |

* A: There was observed the presence of a large quantity of crystalline cellobiose; B: There was observed the presence of a small quantity of crystalline cellobiose; C: There was not observed the presence of any crystalline cellobiose.

As will be seen from the results listed in Table 2, it was confirmed that when the glucose content present in the mixed solution exceeded 50%, cellobiose could not easily be crystallized. In addition, in case of samples which were crystallized after the Brix concentrations thereof were increased, it was found that the cellobiose purity of the resulting crystalline product was decreased. Moreover, the resulting crystals were inspected for the surface structure thereof under a scanning electron microscope and as a result, there was observed such a tendency that the greater the size of crystals, the higher the cellobiose purity thereof.

The foregoing results clearly indicate that highly purified cellobiose can be obtained at a high recovery, when preparing a cellobiose-containing sugar solution having a cellobiose content of not less than 50%, a glucose content of not more than 50% and a Brix concentration falling within the range of from 40 to 50 and using the same as a starting material.

Example 1

A cellobiose-containing sugar solution was prepared from wet pulp according to the method disclosed in the example of Patent Document 4 (JP-A-7-184678). More specifically, an acetic acid buffer having a pH value of 5.5 was added to the wet un-bleached sulfite pulp which was prepared by cooking and digesting a naturally occurring lignocellulose-containing raw material but not drying thereafter, to thus prepare a 2% by mass slurry. Then the slurry thus prepared was introduced into a bio-reactor equipped with a polysulfone membrane whose fractional molecular weight was set at 10,000, the slurry was heated to a temperature of 45° C. while circulating the same with a pump and the cellulase originated from a microorganism belonging to *Trichoderma viride* was then added to the slurry in a concentration of 0.1% by mass on the basis of the total mass of the slurry, while maintaining the slurry at that temperature, to hydrolyze the cellulose through the enzyme reaction which was carried out for 4 hours. The hydrolysis reaction solution which passed through this ultrafiltration membrane was concentrated to thus give a cellobiose-containing sugar solution containing cellobiose in a ratio of 68% relative to the total mass of the saccharides present in the solution.

The resulting cellobiose-containing sugar solution was subjected to a decoloring treatment using activated carbon and then to a deionization treatment by passing the solution through a column packed with an amphoteric ion-exchange resin (available from Organo Corporation). At this stage, the cellobiose concentration of the sugar solution was found to be 70% based on the total solid content and the glucose concentration thereof was found to be 24%. Then the cellobiose-containing sugar solution was further concentrated to give a solution having a concentration of the solid content of 55% and to thus form a slurry containing crystalline cellobiose. The crystalline cellobiose-containing slurry was centrifuged to collect crystals, followed by washing the crystals with a small quantity of water and the subsequent drying of the crystals to thus give crystalline cellobiose having a purity of 95% in a yield of 63% relative to the total amount of cellobiose contained in the original cellobiose-containing sugar solution.

Example 2

To a cellobiose-containing solution or sugar solution prepared by the same method used in Example 1 and having a ratio of cellobiose of 68% with respect to the total amount of the saccharides present therein, there was added glucose to thus prepare a solution having the following saccharide composition: a cellobiose content of 61% and a glucose content of 35%. After the solution was subjected to treatments with activated carbon and an ion-exchange resin, it was concentrated to a concentration of the solid content of 55% to thus give a crystalline cellobiose-containing slurry. The crystalline cellobiose-containing slurry was centrifuged to collect crystals, followed by washing the crystals with a small quantity of water and the subsequent drying of the crystals to thus give cellobiose crystals having a purity of 93% in a yield of 40% relative to the total amount of cellobiose contained in the original cellobiose-containing sugar solution.

Example 3

A cellobiose-containing sugar solution prepared by the same method used in Example 1, which made use of a bioreactor, and having a cellobiose content of 63% with respect to the total amount of the saccharides present therein, was subjected to a continuous concentration treatment using a membrane-concentration system equipped with a loose RO membrane (NTR 7250 available from Nitto Denko Corporation). More specifically, the sugar solution passed through the ultrafiltration membrane of the bio-reactor was continuously supplied to this system, the concentrated solution was thus circulated in this system and the solution passed through the system was then continuously discharged out of the system. The resulting concentrated solution was found to be concentrated to about 12 times. More specifically, the cellobiose content was raised up to 80%, while the initial glucose content of 33% was reduced to 16%. The concentrated solution was then subjected to a decoloring treatment with activated carbon and a desalting treatment with an ion-exchange resin, followed by the concentration thereof to a solid content of 50% to thus give a slurry containing cellobiose crystals. The resulting crystals were recovered and then dried according to the same method used in Example 1 to thus give crystalline cellobiose having a purity of 96% in a yield of 70% relative to the total amount of cellobiose contained in the original cellobiose-containing sugar solution.

Example 4

A cellobiose-containing sugar solution (60 mL having a solid content concentration of 50%) prepared by the same method used in Example 1 and having a cellobiose content of 65% with respect to the total amount of the saccharides present therein, was loaded on a 10 L volume column packed with an Na-type strongly acidic ion-exchange resin (available from Organo Corporation) and then the sugar solution was developed over the column using water at a column temperature of 70° C. and an SV of 1.0 to thus separate the sugar solution into a glucose-containing fraction and a cellobiose-containing fraction. This fractionation resulted in the formation of a cellobiose-containing sugar solution having a cellobiose concentration of 91% based on the total solid content and a glucose concentration of 5% and it was also found that impurities such as salts and proteins were likewise removed from the sugar solution, as well. The cellobiose-containing sugar solution thus prepared was subjected to treatments with activated carbon and an ion-exchange resin by the same methods used in Example 2, followed by the concentration thereof to a solid content of 45% to thus give a crystalline cellobiose-containing slurry. The crystalline cellobiose-containing slurry was centrifuged to collect crystals, followed by the washing of the crystals with a small quantity of water and the subsequent drying of the crystals to thus recover cellobiose crystals having a purity of 98% in a yield of 80%.

Table 3 shows the cellobiose concentrations and glucose concentrations of the cellobiose-containing sugar solutions prepared in Examples 1 to 4 as well as the relation between the purity and recovery of each crystalline product.

TABLE 3

| Cellobiose-Containing Sugar Solution | | Crystals | |
|---|---|---|---|
| Conc. of Cellobiose (%) | Conc. of Glucose (%) | Purity of Cellobiose (%) | Rate of Recovery (%) |
| 61 | 35 | 93 | 40 |
| 70 | 24 | 95 | 63 |
| 80 | 16 | 96 | 70 |
| 91 | 5 | 98 | 80 |

The rate of recovery is expressed in terms of the ratio of crystalline materials recovered relative to the mass of the cellobiose included in the sugar solution prior to the concentration thereof.

The data listed in Table 3 clearly indicate that the reduction of the glucose concentration in the sugar solution permits the considerable improvement of the cellobiose purity and the rate of recovery of the collected crystalline substances and that it is effective for the achievement of a high purity and a high rate of recovery of the crystalline substances to increase, in advance, the cellobiose concentration of the cellobiose-containing sugar solution to a level of not less than 60%. In addition, the foregoing data also indicate that the cellobiose concentration of a cellobiose-containing sugar solution can substantially be increased when removing the glucose present in the cellobiose-containing sugar solution by the concentration of the sugar solution obtained after passing through an ultrafiltration membrane using a loose RO membrane, or by the fractionation of the concentrated sugar solution obtained after passing through an ultrafiltration membrane using a strongly acidic ion-exchange resin. This would be because the foregoing operations and fractionation allow the removal of the glucose present in the sugar solution, simultaneous with the removal of impurities such as salts and proteins possibly present therein.

Example 5

The cellobiose-containing sugar solution having a high content of cellobiose, prepared in Example 4 was concentrated to a solid content concentration of 20%, the sugar solution was then maintained at a temperature of 20° C., 60° C. or 80° C. for one hour and, immediately thereafter, the solution was dried in a spray dryer to thus give cellobiose powder. These powdery cellobiose products were inspected for the solubility in water and the distribution rate of anomers. The results thus obtained are summarized in the following Table 4. In this respect, the distribution rate of anomers was determined using Gas Chromatograph GC14 available from Shimadzu Corporation which was equipped with a column: DB1701 (inner diameter: 0.25 mm; length: 30 m) available from J & W Company. More specifically, each sample (1.0 mg) was dissolved in 0.769 mL of pyridine, 0.077 mL of TMSC and 0.154 mL of HMDS were added to the resulting solution, the mixture was maintained at room temperature for one hour and then it was used in the gas chromatography analysis. In addition, the solubility of each sample in water was expressed in terms of the time required for the complete dissolution of the sample (dissolution time) observed when adding 10 g of the sample to 100 mL of deionized water maintained at 25° C. with stirring (see Table 4). In this connection, the rates of α-anomer and β-anomer observed for the crystals prepared in Example 1 were found to be 7.5% and 92.5%, respectively and the time required for the dissolution thereof was found to be 12.5 minutes.

TABLE 4

| Temp. of Sugar Solution (° C.) | Rate of α-Anomer (%) | Rate of β-Anomer (%) | Dissolution Time (min) |
|---|---|---|---|
| 20 | 12.4 | 87.6 | 8.0 |
| 60 | 23.9 | 76.1 | 4.0 |
| 80 | 44.6 | 55.4 | 2.5 |

It has been confirmed, from the data listed in Table 4, that the drying of the cellobiose-containing sugar solution, while controlling the temperature thereof provides cellobiose powder whose solubility characteristics are improved.

What is claimed is:

1. A method for producing cellobiose with 93% or higher in purity comprising the steps of
    (A) preparing a cellobiose-containing sugar solution;
    (B) adjusting the content of cellobiose present in the sugar solution relative to the total saccharides present therein to at least 60% by mass and the Brix concentration of the sugar solution to 40-50; and
    (C) crystallizing cellobiose present in the sugar solution.

2. The method for producing cellobiose as set forth in claim 1, wherein the step (B) comprises a step of ultrafiltration.

3. The method for producing cellobiose as set forth in claim 2, wherein the step (B) further comprises a step of concentrating the sugar solution through the use of a reverse osmosis membrane after the ultrafiltration step.

4. The method for producing cellobiose as set forth in claim 2, wherein the step (B) further comprises a step of fractionating the sugar solution using a strongly acidic cation-exchange resin after the ultrafiltration step.

5. The method for producing cellobiose as set forth in claim 1, wherein the step (A) comprises the steps of cooking and digesting a raw material containing naturally occurring lignocellulose and then partially hydrolyzing un-dried wet pulp thus obtained by the action of a cellulase.

* * * * *